United States Patent [19]
Rubinfeld et al.

[11] Patent Number: 6,136,846
[45] Date of Patent: Oct. 24, 2000

[54] FORMULATION FOR PACLITAXEL

[75] Inventors: Joseph Rubinfeld, Danville; Ashok Y. Gore, San Ramon; Rajashree Joshi, Union City; Rajesh Shrotriya, Danville, all of Calif.

[73] Assignee: Supergen, Inc., San Ramon, Calif.

[21] Appl. No.: 09/427,153

[22] Filed: Oct. 25, 1999

[51] Int. Cl.$^7$ ............................................ A61K 31/335
[52] U.S. Cl. ............................................ 514/449
[58] Field of Search ............................................ 514/449

[56] References Cited

U.S. PATENT DOCUMENTS

| | | | |
|---|---|---|---|
| 5,504,102 | 4/1996 | Agharkar et al. | 514/449 |
| 5,670,537 | 9/1997 | Canetta et al. | 514/449 |
| 5,681,846 | 10/1997 | Trissel | 514/449 |
| 5,922,754 | 7/1999 | Burchett et al. | 514/449 |
| 5,925,776 | 7/1999 | Nikolayev et al. | 514/449 |
| 6,017,948 | 1/2000 | Rubinfeld et al. | 514/449 |
| 6,046,230 | 4/2000 | Chung et al. | 514/449 |

OTHER PUBLICATIONS

Constantinides, Panayiotis P. et al., "Formulation Development and Antitumor Activity of a Filter–Sterilizable Emulsion of Paclitaxel", *Pharmaceutical Research,* vol. 17, No. 2 (2000), pp. 175–182.

*Primary Examiner*—James H. Reamer
*Attorney, Agent, or Firm*—David J. Weitz; Wilson Sonsini Goodrich & Rosati

[57] ABSTRACT

A pharmaceutical formulation is provided for delivering paclitaxel in vivo comprising: water and micelles comprising paclitaxel and a pharmaceutically-acceptable, water-miscible solubilizer forming the micelles, the solubilizer selected from the group consisting of solubilizers having the general structures $$R_1COOR_2, R_1CONR_2, \text{ and } R_1COR_2,$$

wherein $R_1$ is a hydrophobic $C_3$–$C_{50}$ alkane, alkene or alkyne and $R_2$ is a hydrophilic moiety. The solubilizer is selected such that it does not have a pKa less than about 6.

38 Claims, No Drawings

FORMULATION FOR PACLITAXEL

FIELD OF THE INVENTION

This invention relates to compositions that may be used as pharmaceutical compositions, methods and kits, more particularly to improved pharmaceutical compositions, methods and kits including paclitaxel and pharmaceutically-acceptable, water-miscible solubilizers.

DESCRIPTION OF RELATED ART

Paclitaxel is a unique diterpene anticancer compound derived from the bark of the *Taxus brevifolia* (Pacific yew) tree. A crude extract of the bark demonstrated antineoplastic activity in preclinical tumor screening 30 years ago as part of the National Cancer Institute's (NCI's) large-scale screening program. The active component of the extract, paclitaxel, was isolated and described by M. C. Wani et al, *Plant antitumor agents. VI: The isolation and structure of Paclitaxel. a novel antileukemic and antitumor agent from Taxus brevifolia*, J. Am. Chem. Soc. 93:2325–2327 (1971). This document, and all others referred to herein, are incorporated by reference as if reproduced fully below.

In 1979, Schiff and coworkers rekindled interest in the development of paclitaxel by demonstrating its novel mechanism of action. Paclitaxel stabilizes the tubulin polymer and promotes microtubule assembly, rather than inducing microtubule disassembly like the antimicrotubule agents colchicine, vincristine, and vinblastine. This stabilization results in the inhibition of the normal dynamic reorganization of the microtubule network. Encouraging response rates (complete and partial) have been reported in single-agent phase studies of paclitaxel in breast cancer, previously untreated non-small-cell lung cancer, head and neck cancer, and refractory ovarian cancer.

Unfortunately, paclitaxel is poorly soluble in water (less than 0.01 mg/mL) and other common vehicles used for the parenteral administration of drugs. Certain organic solvents, however, may at least partially dissolve paclitaxel. However, when a water-miscible organic solvent containing paclitaxel at near its saturation solubility is diluted with aqueous infusion fluid, the drug may precipitate.

Solubilization of compounds with surfactants allows for dilution of saturated or near-saturated formulations. Consequently, researchers formulated paclitaxel formulations using 50% Cremophor EU50% dehydrated alcohol (USP, United States Pharmacopoeia), diluted in NS normal saline or D5W (5% dextrose in water) to a final concentration of 5% Cremophor EL and 5% dehydrated alcohol or less, for the intravenous administration of the drug to humans in early clinical trials. (Cremophor EL; Badische Anilin und Soda Fabrik AG [BASF], Ludwigshafen, Federal Republic of Germany). Paclitaxel for injection concentrate is currently available from Bristol-Myers Squibb Co. (New York, N.Y.) in 30-mg (5-mL) single-dose vials. Each milliliter of formulation contains approximately 6 mg Paclitaxel, 527 mg of Cremophor EL, and 49.7% (vol/vol) dehydrated alcohol. This concentrated formulation must be further diluted with NS, D5W, D5NS (normal saline, 5% dextrose in water and 5% dextrose in normal saline) or D5W-R (Ringer's solution with 5% dextrose in water) prior to administration. It has been noted that the Cremophor/Ethanol formulation of paclitaxel precipitates upon dilution with infusion fluid, and fibrous precipitates formed in some compositions during storage for extended periods of time. Additional information regarding Cremophor formulations of paclitaxel may be found in Agharkar et al., U.S. Pat. No. 5,504,102.

An unexpectedly high incidence of serious hypersensitivity reactions was noted in phase I studies of the paclitaxel/Cremophor formulations. D. M. Essayan et al., *Successful Parenteral Desensitization to Paclitaxel*, J. Allergy and Clin. Immun. 97:42–46 (1996). Studies have shown that the Cremophor EL vehicle induces histamine release and hypotension in dogs within 10 minutes of administration.

In January 1985, the NCI sent a letter to all phase I investigators using paclitaxel, directing them to increase the duration of paclitaxel infusions and to pretreat all subjects with antihistamines (both H1 and H2 antagonists) and steroids. The incidence of hyper-sensitivity reactions subsequently decreased. Because the infusion duration was increased and pretreatment medications were added at the same time, it was not possible to determine whether infusion rate or pretreatment was the important factor.

Further studies were carried out in which paclitaxel was administered after premedication with steroids (such as dexamethasone), antihistamines (such as diphenhydramine), and H2-antagonists (such as cimetidine or ranitidine), and the infusion time was extended to 24 hours in an attempt to eliminate the most serious allergic reactions. See Einzig, et al., *Phase II Trial of Taxol in Patients with Metastatic Renal Cell Carcinoma*, Cancer Investigation, 9:133–136 (1991); A. B. Miller et al., *Reporting Results of Cancer Treatment*, Cancer 47:207–214 (1981). Additional description of pre-medication techniques may be found in Carretta et al., U.S. Pat. No. 5,670,537.

There are other disadvantages to using Cremophor formulations as well. Polyvinylchloride (PVC) infusion bags and intravenous administration sets usually contain diethylhexylphthalate (DEHP) as a plasticizer to maximize component flexibility. DEHP leaches to some extent into aqueous infusion fluids and blood products that come in contact with PVC materials. Exposure of animals to chronic high doses (more than 100 mg/kg) of DEHP has resulted in toxic effects including growth retardation, liver weight increase, liver damage, testicular atrophy, teratogenicity, and carcinogenicity. Cosolvents and surfactants may increase the amount of plasticizer leached. Waugh and colleagues evaluated the quantities of DEHP extracted from PVC infusion devices by the commercially available paclitaxel formulation. Substantial quantities of DEHP were extracted by all formulation concentrations tested. Therefore, there is a substantial health risk to patients receiving paclitaxel in the commercially available formulation using conventional PVC-containing equipment.

There is therefore a need for improved formulations comprising paclitaxel, methods of treatment using these formulations and kits comprising these formulations, to overcome the stability problems and to alleviate the clinical side effects of conventional paclitaxel formulations as noted above and as known to one of skill in the art.

SUMMARY OF THE INVENTION

The present invention provides new and improved formulations of paclitaxel, methods of manufacturing these formulations, kits containing these formulations and methods of treating cancer patients using these formulations. The new and improved formulations include pharmaceutically acceptable, water miscible solubilizers other than Cremorphor which are believed to have improved long term stability and reduced adverse effects relative to existing formulations.

In the present invention, a composition for delivering paclitaxel in vivo is provided, which comprises paclitaxel; a solvent; and a pharmaceutically-acceptable, water-miscible solubilizer selected from the group consisting of solubilizers having the general structures:

$R_1COOR_2$, $R_1CONR_2$, and $R_1COR_2$, wherein $R_1$ is a hydrophobic $C_3-C_{50}$ alkane, alkene or alkyne and $R_2$ is a hydrophilic moiety. The solubilizer is selected such that it does not have a pKa less than about 6. Optionally, the solubilizer does not have a pKa less than about 7, more preferably not less than about 8. By designing the solubilizer to not have any acidic hydrogens, potential destabilization of paclitaxel catalyzed by anionic moieties may be reduced. Upon the addition of water, the solubilizer forms micelles within which the paclitaxel is solubilized in the aqueous solution.

The solubilizer may preferably be an ester ($R_1COOR_2$) derived from a lipophilic acid ($R_1COOH$) that has been esterified with a hydrophilic alcohol ($R_2OH$). Examples of the lipophilic acids ($R_1COOH$) include long chain carboxylic acids such as lauric acid, palmitic acid, stearic acid, oleic acid, linoleic acid, archidonic acid, and d-α-tocopheryl acid succinate. Examples of hydrophilic alcohols ($R_2OH$) include polyalcohols such as polyethylene glycols (PEG): PEG 300, 400, and 1000. In a preferred embodiment, the solubilizer is a water miscible vitamin E derivative, and is most preferably d-α-tocopherol polyethylene glycol succinate (TPGS).

The solvent in the composition may be pharmaceutically acceptable, water miscible organic solvent that can dissolve both paclitaxel and the solubilizer. Examples of suitable solvents include alcohols such as ethanol, propylene glycol and benzyl alcohol; polyalcohols such as polyethylene glycol (PEG); and amides such as 2-pyrrolidone, N-methylpyrrolidone and N,N-dimethyl acetamide.

The concentration of paclitaxel in the composition may preferably range from about 5–20 mg/g, more preferably from about 8–15 mg/g, and most preferably from about 10–13 mg/g.

The concentration of solubilzer in the composition may preferably range from about 40–90% w/w, more preferably from 45–75% w/w and most preferably from 50–60% w/w.

The weight ratio of the solubilizer to the solvent may preferably be between about 90:10–40:50, more preferably between about 70:30–45:55, and most preferably about 50:50.

The weight ratio of paclitaxel to the solubilizer may preferably be between about 1:10–1:100, more preferably about 1:20–1:80, and most preferably about 1:30–1:70.

In a preferred embodiment, the composition further comprises an acidifying agent added to the composition in a proportion such that the composition has a resulting pH between about 3 and 5. The acidifying agent may be an organic acid. Examples of organic acid include ascorbic acid, citric acid, tartaric acid, lactic acid, oxalic acid, formic acid, benzene sulphonic acid, benzoic acid, maleic acid, glutamic acid, succinic acid, aspartic acid, diatrizoic acid, and acetic acid. The acidifying agent may also be an inorganic acid, such as hydrochloric acid, sulphuric acid, phosphoric acid, and nitric acid.

Optionally, the solubilizer does not have a hydrogen with a pKa less than about 7, more preferably not less than about 8. By designing the solubilizer to not have any acidic hydrogens, potential destabilization of paclitaxel catalyzed by anionic moieties may be reduced.

The composition may be diluted into aqueous solution by adding saline or other infusion fluid for parenteral administration or intravenous injection.

The composition may optionally be incorporated into a pharmaceutical carrier suitable for oral administration. For example, the composition may be filled into a soft or hard gelatin capsule, or other oral dosage forms. In these oral formulations, polyethylene glycols such as PEG 300 and PEG400 may preferably be used as the solvent for solubilizing paclitaxel, and the concentration of the solvent may preferably be less than about 40% w/w in the finally formed semi-solid or solid composition. These oral formulations may be administered into a host in need thereof, such as a cancer patient.

In another embodiment, a composition is provided which is made by the acts comprising: providing paclitaxel; and combining the paclitaxel with a pharmaceutically-acceptable, water-miscible solubilizer selected from the group consisting of solubilizers having the general structures:

$R_1COOR_2$, $R_1CONR_2$, and $R_1COR_2$, wherein $R_1$ is a hydrophobic $C_3-C_{50}$ alkane, alkene or alkyne and $R_2$ is a hydrophilic moiety. The solubilizer is selected such that it does not have a pKa less than about 6.

In the present invention, a pharmaceutical formulation for delivering paclitaxel in vivo is also provided, which comprises water; and micelles comprising paclitaxel and a pharmaceutically-acceptable, water-miscible solubilizer forming the micelles, the solubilizer selected from the group consisting of solubilizers having the general structures:

$R_1COOR_2$, $R_1CONR_2$, and $R_1COR_2$, wherein $R_1$ is a hydrophobic $C_3-C_{50}$ alkane, alkene or alkyne and $R_2$ is a hydrophilic moiety. The solubilizer is selected such that it does not have a pKa less than about 6.

The solubilizer may preferably be an ester ($R_1COOR_2$) derived from lipophilic acids ($R_1COOH$) that are esterified with a hydrophilic alcohol ($R_2OH$). Examples of the lipophilic acids $R_1COOH$ include long chain carboxylic acids such as lauric acid, palmitic acid, stearic acid, oleic acid, linoleic acid, archidonic acid, and d-α-tocopheryl acid succinate. Examples of hydrophilic alcohols ($R_2OH$) include polyalcohols such as polyethylene glycols (PEG): PEG 300, 400, and 1000. In a preferred embodiment, the solubilizer is a water miscible vitamin E derivatives, and is most preferably d-α-tocopherol polyethylene glycol succinate (TPGS).

The solubilizer contained in both the composition and the pharmaceutical formulation is an amphiphilic ester ($R_1COOR_2$), an amphiphilic amide ($R_1CONR_2$) or an amphiphilic ketone ($R_1COR_2$) which is capable of forming micelle in aqueous solution. Hydrophobic tails ($R_1$) of the solubilizer aggregate with lipophilic paclitaxel while hydrophilic heads ($R_2$) of the solubilizer self-associate in water. Paclitaxel is thus solubized by associating with the hydrophobic tails of the micelles in aqueous solution.

The weight ratio of paclitaxel to the solubilizer may preferably be between about 1:10–1:100, more preferably about 1:20–1:80, and most preferably about 1:30–1:70.

The pharmaceutical formulation or the composition may optionally further include an excipient added to the composition in an amount sufficient to enhance the stability of the composition. Examples of the excipient includes, but are not limited to, cyclodextrin such as α-, β-, and γ-cyclodextrin and modified, amorphous cyclodextrin such as hydroxy-substituted α-, β-, and γ-cyclodextrin.

Another pharmaceutical formulation is also provided, which is made by the acts comprising: providing a stock compostion comprising paclitaxel, a solvent and a pharmaceutically-acceptable, water-miscible solubilizer selected from the group consisting of solubilizers having the general structures:

$R_1COOR_2$, $R_1CONR_2$, and $R_1COR_2$, wherein $R_1$ is a hydrophobic $C_3$–$C_{50}$ alkane, alkene or alkyne and $R_2$ is a hydrophilic moiety, the solubilizer being selected such that it does not have a pKa less than about 6; and combining the composition with an aqueous solution, wherein, upon addition of the aqueous solution, the solubilizer forms micelles within which the paclitaxel is solubilized in the aqueous solution.

One of the advantages of the above-described pharmaceutical formulations and compositions is the use of a non-ionic, amphiphilic solubilizer for paclitaxel. Previously, destabilization of paclitaxel by free carboxylate anion in formulations of Cremorphor occurred. The use of an ester, an amide or a ketone reduces this destabilization. By stabilizing paclitaxel in the composition, the storage shelf life for the composition can be prolonged, while the potency or pharmaceutical activity of the pharmaceutical formulation can be enhanced.

Another advantage of the pharmaceutical formulation is that paclitaxel is entrapped within the micelles formed by the solubilizer. As a result, light-induced damage to paclitaxel may be reduced during the period of infusion.

A further advantage of the pharmaceutical formulation is that the aqueous solution contains paclitaxel-carrying micelles which remain physically and chemically stable. The formulation can be administered intravascularly without undue toxicity from undissolved drug or precipitates of the solubilizer.

A kit containing a pharmaceutical formulation for delivering paclitaxel in vivo is also provided, the pharmaceutical formulation comprising: water and micelles comprising paclitaxel and a pharmaceutically-acceptable, water-miscible solubilizer forming the micelles, the solubilizer having the general structures:

$R_1COOR_2$, $R_1CONR_2$, and $R_1COR_2$, wherein $R_1$ is a hydrophobic $C_3$–$C_{50}$ alkane, alkene or alkyne and $R_2$ is a hydrophilic moiety, the solubilizer being selected such that it does not have a pKa less than about 6.

A method for administering paclitaxel to a host in need thereof is also provided, comprising: providing a pharmaceutical formulation comprising: water and micelles comprising paclitaxel and a pharmaceutically-acceptable, water-miscible solubilizer forming the micelles, the solubilizer selected from the group consisting of solubilizers having the general structures:

$R_1COOR_2$, $R_1CONR_2$, and $R_1COR_2$, wherein $R_1$ is a hydrophobic $C_3$–$C_{50}$ alkane, alkene or alkyne and $R_2$ is a hydrophilic moiety, the solubilizer being selected such that it does not have a pKa less than about 6; and administering the pharmaceutical formulation in a therapeutically effective amount to a host in need thereof.

The method may be used for administering paclitaxel to patients. A wide variety of uses are known for paclitaxel including the treatment of malignant diseases such as cancer including, but not limited to, human ovarian cancer, breast cancer, malignant lymphoma, lung cancer, melanoma, and Kaposi's sarcoma. Other uses of paclitaxel may be developed in the future. The present invention may also intended to be used in conjunction with these future uses of paclitaxel.

DETAILED DESCRIPTION OF THE INVENTION

The present invention provides new and improved formulations of paclitaxel, methods of manufacturing these formulations, kits containing these formulations and methods of treating cancer patients using these formulations. The new and improved formulations include pharmaceutically acceptable, water miscible solubilizers other than Cremorphor and are believed to have improved long term stability and reduced adverse effects relative to existing formulations.

1. Compositions According to the Present Invention

In the present invention, compositions are provided which are used for delivering paclitaxel in vivo. In one embodiment, the composition comprises paclitaxel, a solvent and a pharmaceutically-acceptable, water-miscible solubilizer selected from the group consisting of solubilizers having the general structures:

$R_1COOR_2$, $R_1CONR_2$, and $R_1COR_2$, wherein $R_1$ is a hydrophobic $C_3$–$C_{50}$ alkane, alkene or alkyne and $R_2$ is a hydrophilic moiety, the solubilizer being selected such that it does not have a pKa less than about 6. Upon the addition of water, the solubilizer forms micelles within which the paclitaxel is solubilized in the aqueous solution.

The composition for paclitaxel is formulated based on a combination of a non-ionic, amphiphilic solubilizer that forms micelles to solubilize paclitaxel in an aqueous solution and a solvent that can dissolve paclitaxel and disperse the solubilizer in the composition to form a homogenous composition.

A pharmaceutical formulation can be formed from the composition by adding an aqueous solution such as water, saline or other infusion fluid. When an aqueous solution is added, hydrophobic tails of the solubilizer aggregate with paclitaxel and entrap paclitaxel within a micelle, thereby solubilizing and stabilizing paclitaxel in the resultant pharmaceutical formulation.

In the composition, the solubilizer is an ester, an amide or a ketone with a pKa less than about 6. As a result, the solubilizer is essentially non-ionic under pH 6 in an aqueous solution. Optionally, the solubilizer may be selected such that the solubilizer does not have a pKa less than about 7, more preferably not less than about 8. Maintaining non-ionicity of the solubilzer is believed to prevent destabilization of paclitaxel catalyzed by anions such as carboxylate. to In contrast, the commercially available paclitaxel formulation with 50:50 ethanol: Cremorphor contains carboxylate moieties which ionize and may contribute to the decomposition of paclitaxel in the formulation. The present invention employs an amphiphilic ester as the solubilizer in the composition, carboxylate anion-catalyzed decomposition of paclitaxel may be minimized, thereby enhancing the stability and prolonging storage shelf-life of the drug.

The solubilizer $R_1COOR_2$ may preferably be an ester derived from lipophilic acids ($R_1COOH$) that are esterified with hydrophilic alcohol ($R_2OH$). Examples of lipophilic acids ($R_1COOH$) include long chain carboxylic acids such as lauric acid, palmitic acid, stearic acid, oleic acid, linoleic acid, arachidonic acid, and d-α-tocopheryl acid succinate. Examples of hydrophilic alcohols ($R_2OH$) include polyalcohols such as polyethylene glycols (PEG): PEG 300, 400, and 1000. In a preferred embodiment, the solubilizer is a water miscible vitamin E derivative, and most preferably is d-α-tocopherol polyethylene glycol succinate (TPGS).

The solvent in the composition for delivering paclitaxel in vivo may preferably be pharmaceutically acceptable, water miscible, nonaqueous solvent that can dissolve both paclitaxel and the solubilizer. In the context of this invention, these solvents should be taken to include solvents that are generally acceptable for pharmaceutical use, substantially water-miscible, and substantially non-aqueous. Preferably, these solvents do not cause phthalate plasticizes to leach when the solvents are used with medical equipment whose tubing contains phthalate plasticizers. Preferred examples of the pharmaceutically-acceptable, water-miscible, non-aqueous solvents that may be used in this invention include, but are not limited to, N-methyl pyrrolidone (NMP); propylene glycol; polyethylene glycol (e.g. PEG300, PEG400, etc.); ethyl acetate; dimethyl sulfoxide; dimethyl acetamide; benzyl alcohol; 2-pyrrolidone; benzyl benzoate; $C_{2-6}$ alkanols; 2-ethoxyethanol; alkyl esters such as 2-ethoxyethyl acetate, methyl acetate, ethyl acetate, ethylene glycol diethyl ether, or ethylene glycol dimethyl ether; (s)-(-)-ethyl lactate; acetone; glycerol; alkyl ketones such as methylethyl ketone or dimethyl sulfone; tetrahydrofuran; cyclic alkyl amides such as caprolactam; decylmethylsulfoxide; oleic acid; aromatic amines such as N,N-diethyl-m-toluamide; or 1-dodecylazacycloheptan-2-one.

Most preferred examples of pharmaceutically-acceptable, water-miscible, non-aqueous solvents include alcohols such as ethanol, propylene glycol and benzyl alcohol; polyalcohols such as polyethylene glycol (PEG 300, PEG 400, etc.); and amides such as 2-pyrrolidone, N-methyl-pyrrolidone and N,N-dimethyl acetamide. Additionally, triacetin may also be used as a pharmaceutically-acceptable, water-miscible, non-aqueous solvent, as well as functioning as a solubilizer in certain circumstances.

Pharmaceutical grade paclitaxel suitable for use in this invention may be obtained from a variety of sources, including the National Cancer Institute (Bethesda, Md.). In the context of this invention, paclitaxel is intended to include paclitaxel proper, and paclitaxel derivatives, analogs, metabolites, and prodrugs thereof.

The composition may contain varying amounts of each of the paclitaxel, the pharmaceutically-acceptable, water-miscible solubilizer, solvent, and other ingredients. In a preferred embodiment, the inventive compositions comprise paclitaxel in an amount ranging from about 5–20 mg/g, more preferably from about 8–15 mg/g, and most preferably from about 10–13 mg/g.

In another preferred embodiment, the composition comprises a solubilizer in an amount ranging from about 40–90% w/w, more preferably from 45–75% w/w, and most preferably from 50–60% w/w.

In yet another preferred embodiment, the weight ratio of the solubilizer to the solvent may be between about 90:10–40:50, more preferably between about 70:30–45:55, and most preferably about 50:50.

In yet another preferred embodiment, the weight ratio of paclitaxel to the solubilizer may be between about 1:10–1:100, more preferably about 1:20–1:80, and most preferably about 1:30–1:70.

In yet another preferred embodiment, the composition further comprises an acidifying agent added to the composition in a proportion such that the composition has a resulting pH between about 3 and 5. Adding an acidifying agent to the composition serves to further stabilize the bond to the carbonyl bond of the solubilizer and prevent carbonyl anion-catalyzed decomposition of paclitaxel, if any.

Optionally, the solubilizer does not have a pKa less than about 7, more preferably not less than about 8. By designing the solubilizer not to include a proton doner under physiological conditions, potential destabilization of paclitaxel catalyzed by anionic moieties may be reduced.

The acidifying agent may be an organic acid including, but not limited to, ascorbic acid, citric acid, tartaric acid, lactic acid, oxalic acid, formic acid, benzene sulphonic acid, benzoic acid, maleic acid, glutamic acid, succinic acid, aspartic acid, diatrizoic acid, and acetic acid. The acidifying agent may also be an inorganic acid, including, but not limited to, hydrochloric acid, sulphuric acid, phosphoric acid, and nitric acid. An anhydrous organic acid may preferably be used in a composition that may be further formulated for oral administration, such as incorporation into soft or hard gelatin capsules, tablet or other oral dosage forms.

The amount of acid added to the composition may be sufficient to adjust the pH of the composition at preferably between about pH 3–6, more preferably between about pH 3.5–5, and most preferably between about pH 3–4.

The pharmaceutical formulation or the composition may optionally further include an excipient added to the composition in an amount sufficient to enhance the stability of the composition, maintain the product in solution, or prevent side effects associated with the administration of the inventive composition. Examples of excipients include but are not limited to, cyclodextrin such as α-, β-, and γ-cyclodextrin and modified, amorphous cyclodextrin such as hydroxy-substituted α-, β-, and γ-cyclodextrin. Cyclodextrins such as Encapsin® from Janssen Pharmaceuticals may be used for this purpose.

The composition may be incorporated into a pharmaceutical carrier suitable for oral administration. In a preferred embodiment, polyethylene glycols, such as PEG 300 and 400, may be used as the solvent for their capability of solubilizing paclitaxel and forming semi-solid to solid compositions. In this embodiment, the concentration of polyethylene glycol may preferably be less than about 40% w/w in the finally formed composition. The composition may be filled into a soft or hard gelatin capsule, or another suitable oral dosage form with protective or sustained release coatings and orally administered into a host in need thereof, such as a cancer patient.

The types of protective or sustained release coating that may be used include, but are not limited to, ethylcellulose, hydroxypropylmethylcellulose, hydroxypropylcellulose, hydroxyethylcellulose, and esters of methacrylic and ethacrylic acid (Eudragit RL, RS, and NE polymer products, Rohm Pharma, Darmstadt, Germany). The enteric protective materials or coatings may be, for example, cellulose acetate pthalate, hydroxypropylmethylcellulose, ethylvinylacetate pthalate, polyvinylacetate pthalate and esters of methacrylic and ethacrylic acid (Eudragit S, Eudragit L and Eudragit E30D, Rohm Pharma, Darmstadt, Ger.).

Alternatively, the composition may also be diluted into an aqueous solution to form a pharmaceutical formulation by adding saline or other infusion fluid for parenteral administration or intravenous injection. The pharmaceutical formulation will be described in details below.

2. Pharmaceutical Formulations According to the Present Invention

In the present invention, pharmaceutical formulations for delivering paclitaxel in vivo are also provided, which comprise water and micelles comprising paclitaxel and a pharmaceutically-acceptable, water-miscible solubilizer forming the micelles, the solubilizer selected from the group consisting of solubilizers having the general structures:

wherein $R_1$ is a hydrophobic $C_3$–$C_{50}$ alkane, alkene or alkyne and $R_2$ is a hydrophilic moiety, the solubilizer being selected such that it does not have a pKa less than about 6.

The pharmaceutical formulation can be used for delivering paclitaxel in vivo, preferably via parenteral administration. Parenteral administration has been the preferred approach for paclitaxel as therapy for systemic malignancies. Unfortunately, the currently available paclitaxel formulation which is based on a combination of ethanol and polyoxyethylated castor oil (Cremorphor®, BASF, Germany) may precipitate when added to an infusion fluid. Cremorphor has been associated with a series of clinical side effects necessitating extensive premedication to desensitize the side effects. By contrast, the formulation of the present invention contains a non-ionic ester solubilizer which forms micelles in aqueous solution to solubilize paclitaxel without causing precipitation, and delivers the drug into the body of a host in need.

Generally, micelles can solubilize otherwise insoluble organic material by incorporating the organic material within their hydrophobic interior. The micelle in a pharmaceutical formulation is an association colloid that displays regions of decreasing water solubility going from the outside of the structure to the inside. Micelles are formed by amphiphilic molecules with both hydrophobic and hydrophilic moieties. In the present invention, the solubilizer is an amphiphilic ester with a hydrophobic tail ($R_1$) and a hydrophilic head ($R_2$). The hydrophobic tail of the solubilizer aggregates with lipophilic paclitaxel to form the interior of the micelle while the hydrophilic head ($R_2$) of the solubilizer self-associates with other hydrophilic heads and faces water outside of the micelle. Paclitaxel which is substantially insoluble in aqueous solution is thus solubilized by micelle formation.

The micelles may preferably be non-ionic, such that the head group region of a micelle resembles a concentrated aqueous solution of solute. A non-ionic head group, e.g. sugar or PEG, becomes hydrated by the aqueous solution and solubilizes the micelle. The non-ionic tail group, e.g. long hydrocarbon chain, aggregates with the lipophilic drug via van der Waals interactions, and occupies a range of areas by changing its extended length, compressing or extending its hydrocarbon chain.

The solubilizer ($R_1COOR_2$) may preferably be an ester derived from lipophilic acids ($R_1COOH$) that are esterified with hydrophilic alcohol ($R_2OH$). Examples of the lipophilic acids ($R_1COOH$) include long chain carboxylic acids such as lauric acid, palmitic acid, stearic acid, oleic acid, linoleic acid, arachidonic acid, and d-α-tocopheryl acid succinate. Examples of hydrophilic alcohols ($R_2OH$) include polyalcohols such as polyethylene glycols (PEG): PEG 300, 400, and 1000. In a preferred embodiment, the solubilizer is a water miscible vitamin E derivative, and most preferably is d-α-tocopherol polyethylene glycol succinate (TPGS).

TPGS is derived from vitamin E by esterification of the acid group of d-α-tocopherol succinate with polyethylene glycol. In particular, the commercially available TPGS 1000 esterified with PEG 1000 (Eastman Chemical Company) is water soluble up to approximately 20 wt % and stable under heat sterilization conditions. In addition, the viscosity of TPGS 1000 appears to be constant and low at concentrations below 20 wt %, a desirable property for a pharmaceutical formulation used in parenteral administration.

Other water miscible, amphiphilic solubilizer derived from d- or dl-α-tocopherol may also be used. For example, d- or dl-α-tocopherol may be esterified by water soluble aliphatic dicarboxylic acid such as malonic, succinic, glutaric, adipic, pimelic and maleic acid to form a salt, which is then further esterified with hydrophiles such as PEG to produce water miscible, amphiphilic solubilizers.

In another preferred embodiment, the weight ratio of paclitaxel to the solubilizer may be between about 1:10–1:100, more preferably about 1:20–1:80, and most preferably about 1:30–1:70.

The pharmaceutical formulation can be used for delivering paclitaxel in vivo, preferably via parenteral or intravenous administration. Since the aqueous formulation contains paclitaxel-carrying micelles which remain physically and chemically stable, this formulation can be administered intravascularly without undue toxicity from undissolved drug or precipitates of the solubilizer and still maintains its pharmacological potency. Further, in this formulation, paclitaxel is entrapped within the micelles formed by the solubilizer, thus light-induced damage to paclitaxel may be reduced during the period of infusion.

3. Manufacture of Pharmaceutical Compositions

The present invention also provides a method of manufacture of pharmaceutical compositions. In one embodiment, a pharmaceutical composition is made by the acts comprising: providing paclitaxel; and combining the paclitaxel with a pharmaceutically-acceptable, water-miscible solvent and a pharmaceutically-acceptable, water-miscible solubilizer selected from the group consisting of solubilizers having the general structures:

$R_1COOR_2$, $R_1CONR_2$, and $R_1COR_2$, wherein $R_1$ is a hydrophobic $C_3$–$C_{50}$ alkane, alkene or alkyne and $R_2$ is a hydrophilic moiety, the solubilizer being selected such that it does not have a pKa less than about 6.

In one variation of the embodiment, the pharmaceutical composition may be prepared by dissolving paclitaxel in a small quantity of a pharmaceutically-acceptable, water-miscible solvent with moderate agitation. The volume of the pharmaceutical composition is then made up with the solubilizer dissolved in the solvent and other ingredients and mixed thoroughly.

In another variation of the embodiment, where the pharmaceutical composition further comprises excipients, the excipients, such as hydroxypropyl cyclodextrin, may also be dissolved in an aliquot of the pharmaceutically-acceptable, water-miscible solvent. This aliquot may then be mixed with a premixed solution of paclitaxel and solubilizer as described above. The mixed aliquots are then mixed together, and the remaining volume is made up with the solvent, all under moderate agitation.

In yet another variation of the embodiment, where the pharmaceutical composition further comprises an acidifying agent, the acidifying agent, may be added to the premixed solution of paclitaxel and solubilizer as described above and mixed under moderate agitation. Examples of the acidifying agent include organic acids such as ascorbic acid, citric acid, tartaric acid, lactic acid, oxalic acid, formic acid, benzene sulphonic acid, benzoic acid, maleic acid, glutamic acid, succinic acid, aspartic acid, diatrizoic acid, and acetic acid, and inorganic acids, such as hydrochloric acid, sulphuric acid, phosphoric acid, and nitric acid. The amount of the acidifying agent may be sufficient to adjust the pH of the final formulation to a desired range after dilution of the pharmaceutical composition with infusion fluid, such as saline.

In another embodiment, a pharmaceutical composition is made by the acts comprising: providing a compostion comprising paclitaxel, a solvent and a pharmaceutically-acceptable, water-miscible solubilizer selected from the group consisting of solubilizers having the general structures:

$R_1COOR_2$, $R_1CONR_2$, and $R_1COR_2$, wherein $R_1$ is a hydrophobic $C_3$–$C_{50}$ alkane, alkene or alkyne and $R_2$ is a hydrophilic moiety, the solubilizer being selected such that it does not have a pKa less than about 6; and combining the composition with an aqueous solution, wherein, upon addition of the aqueous solution, the solubilizer forms micelles within which the paclitaxel is solubilized in the aqueous solution.

A kit containing a pharmaceutical formulation for delivering paclitaxel in vivo is also provided, the pharmaceutical formulation comprising: water and micelles comprising paclitaxel and a pharmaceutically-acceptable, water-miscible solubilizer forming the micelles, the solubilizer selected from the group consisting of solubilizers having the general structures:

$R_1COOR_2$, $R_1CONR_2$, and $R_1COR_2$, wherein $R_1$ is a hydrophobic $C_3$–$C_{50}$ alkane, alkene or alkyne and $R_2$ is a hydrophilic moiety, the solubilizer being selected such that it does not have a pKa less than about 6.

4. Method of Administration in Vivo

A method for administering paclitaxel to a host in need thereof is provided, comprising: providing a pharmaceutical formulation comprising: water and micelles comprising paclitaxel and a pharmaceutically-acceptable, water-miscible solubilizer forming the micelles, the solubilizer selected from the group consisting of solubilizers having the general structures:

$R_1COOR_2$, $R_1CONR_2$, and $R_1COR_2$, wherein $R_1$ is a hydrophobic $C_3$–$C_{50}$ alkane, alkene or alkyne and $R_2$ is a hydrophilic moiety, the solubilizer being selected such that it does not have a pKa less than about 6; and administering the pharmaceutical formulation in a therapeutically effective amount to a host in need thereof.

The method may be used for administering paclitaxel parenterally to patients with malignant diseases such as cancer including, but not limited to, human ovarian cancer, breast cancer, malignant lymphoma, lung cancer, melanoma, and Kaposi's sarcoma.

The pharmaceutical formulations according to the invention may be administered in any medically suitable manner, preferably parenterally or orally, more preferably parenterally, and still more preferably intravenously. The pharmaceutical formulation may be prepared by diluting the a composition as described in Section 1 with sterile water, normal saline, D5W, Ringer's solution or other equivalent infusion liquids.

Dilutions of the composition may preferably range from about 5:1 to about 1:10 v/v of the composition to the diluting infusion liquids. The dilutions may also be appropriately adjusted according to specific treatment schemes adopted by clinicians. The ratio of v/v in this context refers to the ratio of the volume of the composition before dilution with the infusion fluids to the total volume of the pharmaceutical formulation following dilution with the infusion fluid. Additionally, the pharmaceutical may be administered in a bolus fashion.

When administering therapeutic agents such as paclitaxel, a highly stable formulation is desirable. Chemical stability of a formulation generally refers to the amount of chemical degradation of a particular agent in the formulation. Chemical stability of a pharmaceutical formulation depends upon the amount of chemical degradation of the active pharmaceutical ingredient in that preparation. Commonly, stability analysis of a pharmaceutical preparation, such as a liquid parenteral product, may be performed under accelerated temperature conditions, such as in a 50° C. oven. For example, stability data for 50° C. for one month can give assurance of stability for a minimum of two years at room temperature. The predictive nature of accelerated stability studies at elevated temperatures is governed by the Arrhenius equation.

Developing formulations of acceptable chemical stability may be important, especially in cases where the composition comprises a cytotoxic drug like the paclitaxel. Physicians will find products which require determining the exact amount of paclitaxel present before using the products undesirable. Additionally, regulatory requirements may specify minimum stability requirements. Therefore, discovery of variables that impact stability is a useful step in development of new pharmaceutical formulations.

Acceptable stability is well understood by one of skill to mean chemical stability that is sufficient for the material to be well accepted in clinical use, that definition being used herein. In a preferred embodiment, the chemical stability of paclitaxel in a 50° C. oven over four weeks is greater than about 85%. In a more preferred embodiment, the chemical stability of paclitaxel in a 50° C. oven over four weeks is greater than about 90%. In a still more preferred embodiment, the chemical stability of paclitaxel in a 50° C. oven over four weeks is greater than about 93%. In a most preferred embodiment, the chemical stability of paclitaxel in a 50° C. oven over four weeks is greater than about 96%.

It will be apparent to those skilled in the art that various modifications and variations can be made in the compositions, kits, and methods of the present invention without departing from the spirit or scope of the invention. Thus, it is intended that the present invention cover the modifications and variations of this invention provided they come within the scope of the appended claims and their equivalents. Additionally, the following examples are appended for the purpose of illustrating the claimed invention, and should not be construed so as to limit the scope of the claimed invention.

EXAMPLES

Example 1

Paclitaxel (10 mg) was dissolved in ethanol. Vitamin E TPGS (VTPGS, 700 mg, Eastman Chemical Company) was melted at 50° C. and dissolved separately in ethanol in a ratio of 3:1, respectively. The paclitaxel and VTPGS solutions were mixed and ethanol was added to the solution to a final amount of 300 mg, resulting in a 7:3 weight ratio of VTPGS to ethanol. Anhydrous ascorbic acid (5 mg) was then added to the mixture. The resultant stock solution (08-A) appears clear and yellow in color. The total volume of the stock solution was 25 mL.

Aliquots of the stock solution (08-A) was transferred into vials at 5 mL/vial, and incubated at 4° C., 25° C., 40° C. and 50° C. respectively for periods of time as listed in Tables 1A, 1B, 1C and 1D. Samples were taken at one week or predetermined intervals and tested for chemical stability. The stability testing was performed using an HPLC method. An LC-F (penta-fluorophenyl bonded phase) 5 μm, 100 Å pore size, 4.6×250 mm column was used. A UV detector set at 227 nm was used. The mobile phase was made up of a 37:58:5 mixture of ACN:Water:MeOH (containing 1 mL/L of $H_3PO_4$). The flow rate was 1.2 minute. The diluent used was acidic methanol (MeOH containing 0.1% acetic acid). The sample concentration was 0.01 mg/mL. The injection volume was 20 µl. The retention time was 14.5 minutes. The results are shown in Tables 1A, 1B, 1C and 1D.

One milliliter of the stock solution (08-A) was diluted to 5.0 mL with 0.9% NaCl and observed for precipitation at room temperature for a period of at least 24 hr. The diluted solution had a pH of about 4. The formulation did not show any signs of precipitation after over 24 hrs, Example 2

Paclitaxel (10 mg) was dissolved in ethanol. Vitamin E TPGS (VTPGS, 600 mg) was melted at 50° C. and dissolved separately in ethanol in a ratio of 3:1, respectively. The paclitaxel and VTPGS solutions were mixed and ethanol was added to the solution to a final amount of 400 mg, resulting in a 6:4 weight ratio of VTPGS to ethanol. Anhydrous ascorbic acid (5 mg) was then added to the mixture. The resultant stock solution (08-B) appears clear and yellow in color. The total volume of the stock solution was 25 mL.

Aliquots of the stock solution (08-B) was transferred into vials at 5 mL/vial, and incubated at 4° C., 25° C., 40° C. and 50° C. respectively for periods of time as listed in Tables 1A, 1B, 1C and 1D. Samples were taken at one week or predetermined intervals and tested for chemical stability of paclitaxel. The stability testing was performed using the method outlined in Example 1. The results are shown in Tables 1A, 1B, 1C and 1D.

One milliliter of the stock solution (08-B) was diluted to 5.0 mL with 0.9% NaCl and observed for precipitation at room temperature for a period of at least 24 hr. The diluted solution had a pH of about 4. The formulation did not show any signs of precipitation after over 24 hrs. or greater.

Example 3

Paclitaxel (10 mg) was dissolved in ethanol. Vitamin E TPGS (VTPGS, 500 mg) was melted at 50° C. and dissolved separately in ethanol in a ratio of 3:1, respectively. The paclitaxel and VTPGS solutions were mixed and ethanol was added to the solution to a final amount of 500 mg, resulting in a 5:5 weight ratio of VTPGS to ethanol. Anhydrous ascorbic acid (5 mg) was then added to the mixture. The resultant stock solution (08-C) appears clear and yellow in color. The total volume of the stock solution was 25 mL.

Aliquots of the stock solution (08-C) was transferred into vials at to 5 mL/vial, and incubated at 4° C., 25° C., 40° C. and 50° C. respectively for periods of time as listed in Tables 1A, 1B, 1C and 1D. Samples were taken at one week intervals and tested for chemical stability of paclitaxel. The stability testing was performed using the method outlined in Example 1. The results are shown in Tables 1A, 1B, 1C and 1D.

One milliliter of the stock solution (08-C) was diluted to 5.0 mL with 0.9% NaCl and observed for precipitation at room temperature for a period of at least 24 hr. The diluted solution had a pH of about 4. The formulation did not show any signs of precipitation after over 24 hrs.

TABLE 1A

| Time (month at 4° C.) | 08-A | 08-B | 08-C |
|---|---|---|---|
| | (% Paclitaxel Remaining) | | |
| 0 | 100 | 100 | 100 |
| 1 | 99 | 102 | 103 |
| 3 | 103 | 103 | 104 |

TABLE 1B

| Time (month at 25° C.) | 08-A | 08-B | 08-C |
|---|---|---|---|
| | (% Paclitaxel Remaining) | | |
| 0 | 100 | 100 | 100 |
| 1 | 99 | 99 | 101 |
| 2 | 98 | 99 | 101 |
| 3 | 101 | 102 | 104 |

TABLE 1C

| Time (week at 40° C.) | 08-A | 08-B | 08-C |
|---|---|---|---|
| | (% Paclitaxel Remaining) | | |
| 0 | 100 | 100 | 100 |
| 2 | 100 | 101 | 101 |
| 4 | 97 | 98 | 100 |
| 12 | 102 | 103 | 104 |

TABLE 1D

| Time (week at 50° C.) | 08-A | 08-B | 08-C |
|---|---|---|---|
| | (% Paclitaxel Remaining) | | |
| 0 | 100 | 100 | 100 |
| 1 | 98 | 100 | 101 |
| 2 | 100 | 101 | 100 |
| 3 | 97 | 98 | 100 |
| 4 | 96 | 100 | 101 |

Example 4

Chemical and physical stability of the paclitaxel formulation following dilution with normal saline was determined at certain time points after the dilution. Table 2 lists percentages of paclitaxel at indicated time points for a period of 24 hr. after 1:10 dilution of two paclitaxel formulations: paclitaxel at 10 mg/g in 50:50 ethanol: vitamin E TPGS, and paclitaxel at 12.5 mg/g in 50:50 ethanol:vitamin E TPGS.

TABLE 2

| Paclitaxel (10.06 mg/g), at 1:10 dilution (1.01 mg/g) | | Paclitaxel (12.44 mg/g), at 1:10 dilution (1.24 mg/g) | |
|---|---|---|---|
| Time (hr) | % Paclitaxel remaining | Time (hr) | % Paclitaxel remaining |
| 0 | 99.74 | 0 | 99.96 |
| 2 | 99.73 | 2 | 99.81 |
| 4 | 99.44 | 4 | 99.54 |
| 8 | 99.55 | 8 | 99.17 |
| 24 | 99.16 | 24 | 99.61 |

Table 3 lists observation of precipitation at indicated time points after dilution of the paclitaxel formulation according the present invention with normal saline at indicated ratios. The paclitaxel formulation has paclitaxel at 12.5 mg/g in 50:50 ethanol:vitamin E TPGS.

TABLE 3

| Dilution Ratio | Precipitation after (hr) | | | | |
|---|---|---|---|---|---|
| | 0 | 24 | 32 | 47 | 71 |
| 1:5 | None | None | Yes | Yes | Yes |
| 1:6 | None | None | Yes | Yes | Yes |
| 1:7 | None | None | Yes | Yes | Yes |

TABLE 3-continued

| Dilution Ratio | Precipitation after (hr) | | | | |
|---|---|---|---|---|---|
| | 0 | 24 | 32 | 47 | 71 |
| 1:8 | None | None | None | Yes | Yes |
| 1:9 | None | None | None | None | Yes |
| 1:10 | None | None | None | None | Yes |

What is claimed is:

1. A composition for delivering paclitaxel in vivo comprising:
   paclitaxel;
   a solvent; and
   a pharmaceutically-acceptable, water-miscible solubilizer selected from the group consisting of solubilizers having the general structures $R_1COOR_2$, $R_1CONR_2$, and $R_1COR_2$, wherein $R_1$ is a derivative of d-α-tocopherol and $R_2$ is a hydrophilic moiety.

2. The composition according to claim 1 wherein, upon the addition of water, the solubilizer forms micelles within which the paclitaxel is solubilized in the aqueous solution.

3. The composition according to claim 1 wherein the derivative of d-α-tocopherol is esterified by polyethylene glycol.

4. The composition according to claim 1 wherein the solubilizer is esterified d-α-tocopheryl acid succinate.

5. The composition according to claim 1 wherein the solubilizer is d-α-tocopherol polyethylene glycol succinate (TPGS).

6. The composition according to claim 1 wherein the solvent is an alcohol.

7. The composition according to claim 1 wherein the solvent is selected from the group consisting of ethanol, propylene glycol, benzyl alcohol, polyethylene glycol (PEG).

8. The composition according to claim 1 wherein the solvent is an amide.

9. The composition according to claim 1 wherein the solvent is selected from the group consisting of 2-pyrrolidone, N-methyl-pyrrolidone and N,N-dimethyl acetamide.

10. The composition according to claim 1 wherein the concentration of solubilzer in the composition is between about 40% w/w and 90% w/w.

11. The composition according to claim 1 wherein the concentration of solubilzer in the composition is between about 45% w/w and 75% w/w.

12. The composition according to claim 1 wherein the concentration of solubilzer in the composition is between about 50% w/w and 60% w/w.

13. The composition according to claim 1 wherein the weight ratio of the solubilizer to the solvent is between about 90:10 and 40:60.

14. The composition according to claim 1 wherein the weight ratio of the solubilizer to the solvent is between about 70:30 and 45:55.

15. The composition according to claim 1 wherein the weight ratio of the solubilizer to the solvent is about 50:50.

16. The composition according to claim 1, further comprising an acidifying agent.

17. The composition according to claim 16 wherein the acidifying agent is at a concentration sufficient to result in a pH between about 3 and 6.

18. The composition according to claim 16 wherein the acidifying agent is at a concentration sufficient to result in a pH between about 4 and 5.

19. The composition according to claim 16 wherein the acidify agent is selected from the group consisting of ascorbic acid, citric acid, tartaric acid, lactic acid, oxalic acid, formic acid, benzene sulphonic acid, benzoic acid, maleic acid, glutamic acid, succinic acid, aspartic acid, diatrizoic acid, acetic acid, hydrochloric acid, sulphuric acid, phosphoric acid, and nitric acid.

20. A composition made by the act comprising:
   combining paclitaxel with a pharmaceutically-acceptable, water-miscible solubilizer selected from the group consisting of solubilizers having the general structures $R_1COOR_2$, $R_1CONR_2$, and $R_1COR_2$, wherein $R_1$ is a derivative of d-α-tocopherol and $R_2$ is a hydrophilic moiety.

21. A pharmaceutical formulation for delivering paclitaxel in vivo comprising:
   water; and
   micelles comprising paclitaxel and a pharmaceutically-acceptable, water-miscible solubilizer forming the micelles, the solubilizer selected from the group consisting of solubilizers having the general structures $R_1COOR_2$, $R_1CONR_2$, and $R_1COR_2$, wherein $R_1$ is a derivative of d-α-tocopherol and $R_2$ is a hydrophilic moiety.

22. The pharmaceutical formulation according to claim 21 wherein the solubilizer is esterified by polyethylene glycol.

23. The pharmaceutical formulation according to claim 21 wherein the solubilizer is d-α-tocopheryl acid succinate.

24. The pharmaceutical formulation according to claim 21 wherein the solubilizer is d-α-tocopherol polyethylene glycol succinate (TPGS).

25. The composition according to claim 21 wherein the concentration of solubilzer in the composition is between about 40% w/w and 90% w/w.

26. The composition according to claim 21 wherein the concentration of solubilzer in the composition is between about 45% w/w and 75% w/w.

27. The composition according to claim 21 wherein the concentration of solubilzer in the composition is between about 50% w/w and 60% w/w.

28. The composition according to claim 21 wherein the weight ratio of the solubilizer to the solvent is between about 90:10 and 40:60.

29. The composition according to claim 21 wherein the weight ratio of the solubilizer to the solvent is between about 70:30 and 45:55.

30. The composition according to claim 21 wherein the weight ratio of the solubilizer to the solvent is about 50:50.

31. The pharmaceutical formulation according to claim 21 further including an excipient.

32. The pharmaceutical formulation according to claim 31 where the excipient is selected from the group consisting of α-, β-, γ-cyclodextrin, and amorphous cyclodextrin.

33. A pharmaceutical formulation made by the acts comprising:
   providing a composition comprising paclitaxel, a solvent and a pharmaceutically-acceptable, water-miscible solubilizer selected from the group consisting of solubilizers having the general structures $R_1COOR_2$, $R_1CONR_2$, and $R_1COR_2$, wherein $R_1$ is a derivative of d-α-tocopherol and $R_2$ is a hydrophilic moiety; and combining the composition with an aqueous solution, wherein, upon addition of the aqueous solution, the solubilizer forms micelles within which the paclitaxel is solubilized in the aqueous solution.

34. A kit containing a pharmaceutical formulation wherein the pharmaceutical formulation comprising:

water; and micelles comprising paclitaxel and a pharmaceutically-acceptable, water-miscible solubilizer forming the micelles, the solubilizer selected from the group consisting of solubilizers having the general structures $R_1COOR_2$, $R_1CONR_2$, and $R_1COR_2$, wherein $R_1$ is a derivative of d-α-tocopherol and $R_2$ is a hydrophilic moiety.

35. A method for administering paclitaxel to a host in need thereof comprising:

providing a pharmaceutical formulation comprising: water and micelles comprising paclitaxel and a pharmaceutically-acceptable, water-miscible solubilizer forming the micelles, the solubilizer selected from the group consisting of solubilizers having the general structures $R_1COOR_2$, $R_1CONR_2$, and $R_1COR_2$, wherein $R_1$ is a derivative of d-α-tocopherol and $R_2$ is a hydrophilic moiety; and administering the pharmaceutical formulation in a therapeutically effective amount to a host in need thereof.

36. A composition according to claim 1 wherein paclitaxel has a concentration in the composition between 5 and 20 mg/g.

37. A composition according to claim 1 wherein paclitaxel has a concentration in the composition between 8 and 15 mg/g.

38. A composition according to claim 1 wherein paclitaxel has a concentration in the composition between 10 and 13 mg/g.

* * * * *

UNITED STATES PATENT AND TRADEMARK OFFICE
CERTIFICATE OF CORRECTION

PATENT NO. : 6,136,846
DATED : October 24, 2000
INVENTOR(S) : Rubinfeld et al.

It is certified that error appears in the above-identified patent and that said Letters Patent is hereby corrected as shown below:

<u>Title page,</u>
Item [75] Inventors: please insert: -- Rajashree Joshi, Ashok Y. Gore, Joseph Rubinfeld, Rajesh Shrotriya --.

Signed and Sealed this

Fifth Day of March, 2002

Attest:

JAMES E. ROGAN
*Attesting Officer*     *Director of the United States Patent and Trademark Office*